United States Patent [19]

Waldmann et al.

[11] Patent Number: 5,434,310
[45] Date of Patent: Jul. 18, 1995

[54] PROCESS FOR THE PREPARATION OF ACYLBENZENES

[75] Inventors: Helmut Waldmann; Manfred Hajek, both of Leverkusen; Otto Immel, Krefeld; Lothar Puppe, Burscheid; Rudolf Braden, Odenthal, all of Germany

[73] Assignee: Bayer Aktiengesellschaft, Leverkusen, Germany

[21] Appl. No.: 180,516

[22] Filed: Jan. 12, 1994

Related U.S. Application Data

[63] Continuation of Ser. No. 980,147, Nov. 23, 1992, abandoned, which is a continuation of Ser. No. 748,606, Aug. 22, 1991, abandoned.

[30] Foreign Application Priority Data

Aug. 29, 1990 [DE] Germany .............. 4027276

[51] Int. Cl.⁶ .................. C07C 45/45
[52] U.S. Cl. .................. 568/319
[58] Field of Search ........... 568/322, 323, 319, 22, 568/23

[56] References Cited

U.S. PATENT DOCUMENTS

| 4,652,683 | 3/1987 | Nicolau et al. | 568/319 |
| 4,668,826 | 5/1987 | Gupta, I | 568/319 |
| 4,714,781 | 12/1987 | Gupta, II | 568/319 |
| 4,960,943 | 10/1990 | Batta et al. | 568/319 |

FOREIGN PATENT DOCUMENTS

| 0239383 | 9/1987 | European Pat. Off. | 568/319 |
| 0279322 | 8/1988 | European Pat. Off. | 568/319 |
| 2592039 | 6/1987 | France | 568/319 |
| 2616583 | 10/1976 | Germany | 568/319 |

OTHER PUBLICATIONS

Friedel-Crafts and Related Reactions, G. A. Olah (ed.), Interscience Publishers, 1963, pp. 34, 35, 96, 97.
Mechanism and Structure in Organic Chemistry, E. S. Gould (ed.), Henry Holt and Company, 1959, pp. 428 and 429.
Knoche et al., J. Am. Chem. Soc., 110:7484–7489 (1988).

*Primary Examiner*—James H. Reamer
*Attorney, Agent, or Firm*—Sprung Horn Kramer & Woods

[57] ABSTRACT

Acylbenzenes of the formula

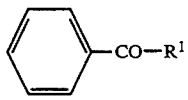 (I)

can be prepared by reaction of benzene with carboxylic acids of the formula $$HOOC-R^1 \quad \text{(II)}$$

where $R^1$ has the meaning given in the text, using a molar ratio of benzene:carboxylic acid=1–50:1 at a temperature of 200°–400° C., a zeolite of the Pentasil type having an $SiO_2/M^2O_2$ ratio of 15–500:1 being used as acid catalyst; in the latter formula, $M^2$ is one element or more from the group comprising Al, B, Ga, In, Fe, Cr, V, As and Sb.

8 Claims, No Drawings

PROCESS FOR THE PREPARATION OF ACYLBENZENES

This application is a continuation of application Ser. No. 07/980,147, filed Nov. 23, 1992 now abandoned, which is a continuation of application Ser. No. 07/748,606, filed Aug. 22, 1991 now abandoned.

BACKGROUND OF THE INVENTION

1. Field of the Invention

The invention relates to a process for the preparation of acylbenzenes by reaction of benzene with carboxylic acids on acid catalysts.

Acylbenzenes are intermediates which can be widely employed for the synthesis of active compounds in the field of medicaments and plant protection. Benzophenone is used, in addition, in relatively large amounts as odour-fixing agent for perfumes and soaps.

2. Description of the Related Art

Acylbenzenes are generally prepared by acylation of benzene with acyl chlorides using Friedel-Crafts catalysts such as aluminium chloride, zinc chloride, iron chloride and similar metal halides known to those skilled in the art. These Friedel-Crafts catalysts are generally required in stoichiometric amounts. During the workup of acylation mixtures of this type the Friedel-Crafts catalysts are destroyed by hydrolysis and produce relatively large amounts of hydrochloric acid in the off-gas or in the effluent. This hydrochloric acid, which has to be disposed of, originates both from the catalyst and also from the acyl chloride employed for the acylation. In addition to this disposal as a considerable environmental problem, the corrosion problem, which is also caused by the hydrochloric acid, must also be solved. The aim is, therefore, to find a process which is both environmentally friendly and also inexpensive with respect to the disadvantages indicated.

A first attempt to achieve this aim is described in German Offenlegungsschrift 26 16 583, in which it is proposed to prepare aryl ketones by reaction of non-hydroxylated aromatic compounds with a carboxylic acid or a carboxylic acid anhydride in the vapour phase at 250° to 500° C. in the presence of an acid silica/alumina catalyst having a surface area of at least 50 m³/g. However, with this process using amorphous or crystalline silica/alumina catalysts undesired by-products of very different structures are formed, for example in the case of the reaction of benzene with benzoic acid, biphenyl, diphenylmethane and alkylated benzenes are also formed in addition to the desired benzophenone.

A particularly serious disadvantage of this process is the short life of the catalysts; thus, on comparison of Examples 2 and 3 of German Offenlegungsschrift 26 16 583, the amount of the desired benzophenone drops considerably if the reaction time is increased to 24 h.

SUMMARY OF THE INVENTION

It has now been found that when selected defined zeolites are employed, improved selectivities and considerably longer service lives can be achieved. Selected catalysts of this type are the zeolites of the Pentasil type described in detail below.

A process has been found for the preparation of acylbenzenes of the formula

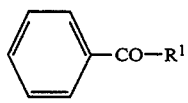

in which
R$^1$ represents methyl, ethyl, isopropyl, straight-chain C$_3$–C$_{14}$-alkyl or —C$_6$H$_4$—R$^2$, in which R$^2$ denotes hydrogen, methyl, ethyl, isopropyl or straight-chain C$_3$–C$_{14}$-alkyl, by reaction of benzene with carboxylic acids on acid catalysts, which is characterised in that a carboxylic acid of the formula $$HOOC\text{—}R^1 \qquad (II)$$

in which R$^1$ has the above meaning, is reacted, in the free form or in the form of its anhydride or ester, with benzene in a molar ratio of benzene:carboxylic acid = 1–50:1 at a temperature of 200°–400° C. and the acid catalyst used is a zeolite of the Pentasil type having an SiO$_2$/M$^2$O$_2$ ratio of 15–500:1, M$^2$ representing one element or more from the group comprising Al, B, Ga, In, Fe, Cr, V, As and Sb in trivalent form.

DETAILED DESCRIPTION OF THE INVENTION

The process according to the invention is equally suitable for the reaction of aliphatic and aromatic carboxylic acids.

Examples which may be mentioned of straight-chain C$_3$–C$_{14}$-alkyl are n-propyl, n-butyl, n-hexyl, n-octyl, n-decyl, n-dodecyl or n-tetradecyl.

Carboxylic acids of the formula (I) in which R$^1$ represents methyl, ethyl, n-propyl, isopropyl or —C$_6$H$_4$—R$^2$, in which R$^2$ denotes hydrogen, methyl or ethyl, are particularly suitable for the process according to the invention. Acetic acid and benzoic acid are particularly preferably suitable. The preparation of benzophenone from benzene and benzoic acid by the process according to the invention may be mentioned in particular.

The acids can be employed either in free form in accordance with formula (II) or in the form of their anhydrides or their esters. Esters which may be mentioned are, preferably, the methyl or ethyl esters.

Benzene is employed in an at least equimolar ratio with respect to the carboxylic acid. Preferably, however, an excess of benzene is used, for example in a molar ratio of benzene:carboxylic acid = 5–30, particularly preferably = 10–20.

The process according to the invention is characterised in particular by the use of a zeolite of the Pentasil type as catalyst.

Zeolites are characterised by the general formula (III):

$$M^1{}_m[mM^2O_2 \cdot nSiO_2] \cdot qH_2O \qquad (III)$$

In this formula
M$^1$ denotes an equivalent of an exchangeable cation, the number m of which corresponds to the proportion of M$^2$;
M$^2$ denotes a trivalent element, which together with the Si forms the oxide skeleton of the zeolite;
n/m denotes the SiO$_2$M$^2$O$_2$ ratio; and
q denotes the amount of adsorbed water.

On the basis of their basic structure, zeolites are crystalline aluminosilicates which are built up of a network of $SiO_4$ and $M^2O_4$ tetrahedra. The individual tetrahedra are linked to one another by oxygen bridges via the corners of the tetrahedra and form a spatial network which has channels and cavities running through it uniformly. The individual zeolite structures differ in the arrangement and size of the channels and cavities and also in their composition. Exchangeable cations are incorporated as compensation for the negative charge of the lattice, which results from the proportion of $M^2$. The adsorbed aqueous phase q $H_2O$ is reversibly removable without the skeleton losing its structure.

$M^2$ is frequently aluminium, but can also be partially or entirely replaced by other trivalent elements.

A detailed description of zeolites is given, for example, in the monograph by D. W. Breck "Zeolite Molecular Sieves, Structure, Chemistry, and Use", J. Wiley & Sons, New York, 1974. A further description, in particular of the zeolites richer in $SiO_2$, which are of particular interest for catalytic use, is given in the monograph by P. A. Jacobs and J. A. Martens "Synthesis of High-Silica Aluminosilicate Zeolites", Studies in Surface Science and Catalysis Ed. B. Delmon and J. T. Yates, Elsevier, Amsterdam-Oxford-New York-Tokyo 1987.

The zeolites which can be employed according to the invention belong to the Pentasil type; they are medium-pored with pore widths of approximately 5 Å.

Amongst the Pentasil types, the zeolite structures ZSM 5, ZSM 11, ZSM 8, ZSM 5/ZSM 11 intermediates, Zeta 1, Zeta 2, ZBM 10, Ultrasil, Ultrazel, TZ-01, NU-4, NU-5, AZ 1 or a mixture of several of these are preferably employed. Particularly preferably, the zeolite structures ZSM 5, ZSM 11, ZSM 8 and ZSM 5/ZSM 11 are employed.

In the said zeolite structures, $M^2$ is one element or more from the group comprising Al, B, Ga, In, Fe, Cr, V, As and Sb, preferably one element or more from the group Al, B, Ga and Fe.

Exchangeable cations $M^1$ which the said zeolites can contain are, for example, those of Li, Na, K, Mg, Ca, Cu, Zn, rare earth metals, Ti, Zr, Sn, Cr, Fe, Mn, Co, Ni and others. Those zeolites of the Pentasil type in which at least some of the metal cations, preferably 50–100% and particularly preferably 80–100% of all metal cations originally present, have been replaced by hydrogen ions are preferred according to the invention. Pentasil zeolites which are completely in the $H^+$ form, as far as this is technically possible, are very particularly preferred. The acid $H^+$ forms of the zeolites are preferably prepared by replacing metal ions by ammonium ions and subsequently calcining the zeolite in which this replacement has been made. A further possibility for the replacement consists, in the case of zeolites which have an n/m value of at least 5, in carrying out the proton replacement using mineral acids. The $H^+$ forms, in which the replacement is complete, of the zeolites of the Pentasil type are very particularly preferably employed.

Whilst the $SiO_2/M^2O_2$ ratio n/m defined in formula (III) can quite generally assume values of 1 to 3000 or above in zeolites, for the process according to the invention zeolites of the Pentasil type in which n/m assumes values of 15–500 are employed. Preferably, n/m values of 30 300 and very particularly preferably those of 50–150 are used. If the ratio $SiO_2/M^2O_2$ is replaced by the expression $SiO_2/M^2{}_2O_3$, the values of n/m are doubled.

The feed products can be supplied to the catalyst in gas form or all or some of them can also be in liquid form. When the starting materials are used in liquid form the so-called trickle phase can be used in particular. Preferably, however, both the benzene and the carboxylic acid are employed in gas form. For this purpose a temperature in the range of 200° to 400° C., preferably 250° to 300° C., is chosen. The reaction described still takes place even at temperatures below or above these values, but a reduced reaction rate or the occurrence of by-products must be expected.

The reaction pressure is of minor significance for the process according to the invention. Thus, a reduced pressure can be employed in particular in order to facilitate a reaction in the gas phase in the case of high-boiling feed materials; on the other hand, a pressure higher than atmospheric pressure makes a higher space yield possible. However, because of the simpler implementation from the standpoint of process technology, the process will be carried out in the vicinity of atmospheric pressure if possible.

The zeolite catalyst can be arranged in a fixed bed; however, it can also be employed in the form of a moving or fluidized bed. In the case of reactions in condensed phase, the catalyst can be either suspended or fixed in a cage. Suitable industrial reactors are shell-and-tube reactors, shaft furnaces, tray reactors or fluidized bed reactors. Shell-and-tube reactors have proved particularly suitable as reactors for the process according to the invention.

In the reaction of the process according to the invention very small amounts of, and in many cases virtually no, condensable volatile by-products are formed. However, at temperatures at the upper edge of the range described some $CO_2$ does form, which presumably forms as a result of decarboxylation of the carboxylic acid. It is therefore advantageous to operate at a temperature in the middle or lower part of the indicated range and in this case to accept an only partial conversion of the carboxylic acid. In general, the conditions are chosen such that 5–50% of the carboxylic acid employed is reacted.

Thus, for example, in the case of the reaction of benzene with benzoic acid the process is carried out with a benzoic acid conversion of 20–40% of the benzoic acid employed.

If the reactivity declines, the catalyst can be reactivated by known methods, say by burning-off with air or other oxygen-containing gas mixtures.

In a particular embodiment, ZSM-5 in the $H^+$ form with a $SiO_2/Al_2O_3$ ratio of 100–300:1 is used in the reaction tube for carrying out the reaction in the gas phase. Reaction tubes of this type have diameters of 20 to 40 mm and lengths of 1 to 6 m. Benzene in vapour form and the vapourised carboxylic acid, if appropriate in a gentle stream of inert gas, are passed over the catalyst arranged in this way. A particularly preferred temperature in this case is the range from 250°–280° C. Suitable inert gases are nitrogen, noble gases and others. The mixture leaving the catalyst zone is condensed and worked up in a manner known per se.

For workup it is possible, for example, to condense the entire product stream, from which the carboxylic acid, for example the benzoic acid, is crystallised. The crystalline material can then be separated off by mechanical means and the mother liquor is freed from excess benzene by distillation. A crude acylbenzene is obtained as residue and can be further purified by distillation or crystallisation. However, it is also possible to partially condense the product stream and in this way separate the benzene, the unconverted carboxylic acid and the acylbenzene by fractionation. In many cases an integral condensation of the product stream and a subsequent fractionation are suitable. Unconverted benzene and unconverted carboxylic acid can be recycled into the reaction in a known manner.

EXAMPLES

Example 1

100 g/h of benzene vapour and 10 g/h of liquid benzoic acid are passed under a gentle $N_2$ stream into a quartz tube which has a diameter of 20 mm and a length of 560 mm and is filled with 50 g of HZSM-5 with various $SiO_2/Al_2O_3$ ratios. The reaction gases flowing out are condensed and the condensed phase is analysed by gas chromatography after distilling of the excess benzene.

The following results are obtained:

| H-ZSM 5 catalyst $SiO_2/Al_2O_3$ | Temperature [°C.] | Benzoic acid [% by weight] in the produc | Benzophenone [% by weight] in the product |
|---|---|---|---|
| 30 | 200 | 98.53 | 1.87 |
| | 250 | 95.91 | 4.09 |
| | 300 | 95.45 | 4.55 |
| | 330 | 90.70 | 9.30 |
| 100 | 200 | 94.75 | 5.25 |
| | 250 | 85.32 | 14.68 |
| | 300 | 68.52 | 31.48 |
| | 330 | 74.35 | 25.27 |
| 272 | 250 | 78.91 | 21.09 |
| | 280 | 72.22 | 27.78 |
| 800 | 250 | 97.76 | 2.24 |
| | 300 | 93.63 | 6.37 |
| | 330 | 80.80 | 19.20 |
| | 350 | 62.54 | 37.46 |

Example 2

Analogously to the procedure according to Example 1, the following results are obtained using 10 g/h of acetic acid in place of benzoic acid:

| H-ZSM 5 catalyst $SiO_2/Al_2O_3$ | Temperature [°C.] | Acetic acid [% by weight] in the product | Acetophenone [% by weight] in the product |
|---|---|---|---|
| 272 | 200 | 0 | 0 |
| | 250 | 95.1 | 4.9 |
| | 280 | 97.62 | 1.68* |
| 800 | 200 | 0 | 0 |
| | 250 | 99.69 | 0.31 |
| | 300 | 97.23 | 2.51* |

*)Remainder consists of unidentified by-products

Example 3 (for comparison)

Using a procedure as in Example 1 at 300° C., the following zeolites were employed in place of ZSM 5 catalysts:

a) mordenite, containing 30% by weight of aluminium oxide, granulated, and b) faujasite (zeolite Y), containing 30% by weight of aluminium oxide, granulated.

Using 20 g of benzoic acid, dissolved in 200 g of benzene, the following were obtained:

in case a): after distilling off excess benzene, 20.6 g of residue consisting of 95.7% by weight of benzoic acid and 4.3% by weight of benzophenone, and in case b): 20.0 g of residue consisting of 97.9% by weight of benzoic acid and 2.1% by weight of benzophenone.

What is claimed is:

1. A process for the preparation of an acylbenzene of the formula:

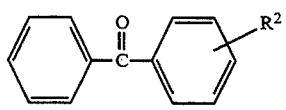

wherein

R² represents hydrogen, methyl, ethyl, isopropyl or straight-chain $C_{3-4}$-alkyl;

said process comprising reacting benzene with the free form of a carboxylic acid of the formula:

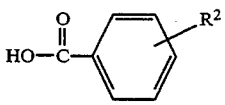

on an acid catalyst, in the gas phase, in a molar ratio of benzene:carboxylic acid of 1–50:1, and at a temperature of 250°–400° C., and wherein said acid catalyst is a zeolite of the Pentasil type selected from the group consisting of:

(i) $M^1$/Al/Si-zeolites having an $SiO_2$:$AlO_2$ ratio of 50–150:1, wherein $M^1$ represents an alkaline earth metal cation; and (ii) $M^{1'}$/$M^2$/Si-zeolites having an $SiO_2$:$M^2O_2$ ratio of 50–150:1, wherein $M^{1'}$ represents H+ or an equivalent of an exchangeable cation and $M^2$ represents a trivalent atom selected from the group consisting of B, Ga, In, Fe, Cr, V, As and Sb.

2. The process according to claim 1, wherein the zeolite is a $M^1$/Al/Si-zeolite.

3. The process of claim 1, wherein the molar ratio of benzene:carboxylic acid is 5–30:1.

4. The process of claim 3, wherein the molar ratio of benzene:carboxylic acid is 10–20:1.

5. The process of claim 1, wherein benzene and benzoic acid are reacted to give benzophenone.

6. The process of claim 5, wherein the reaction is carried out at 250°–300° C. up to a benzoic acid conversion of 20–40% of the benzoic acid employed.

7. The process of claim 1, wherein $M^2$ represents one element or more from the group comprising Al, B, Ga, and Fe.

8. The process according to claim 1, wherein the reaction is carried out at a temperature of 250°–300° C.

* * * * *